(12) United States Patent
Harper et al.

(10) Patent No.: US 12,084,658 B2
(45) Date of Patent: Sep. 10, 2024

(54) RECOMBINANT VIRUS PRODUCTS AND METHODS FOR INDUCING DUX4 EXON SKIPPING

(71) Applicant: RESEARCH INSTITUTE AT NATIONWIDE CHILDREN'S HOSPITAL, Columbus, OH (US)

(72) Inventors: Scott Quenton Harper, Powell, OH (US); Nicolas Sebastien Wein, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 290 days.

(21) Appl. No.: 17/500,410

(22) Filed: Oct. 13, 2021

(65) Prior Publication Data

US 2022/0267768 A1 Aug. 25, 2022

Related U.S. Application Data

(63) Continuation of application No. 16/079,426, filed as application No. PCT/US2017/019422 on Feb. 24, 2017, now Pat. No. 11,180,755.

(60) Provisional application No. 62/300,500, filed on Feb. 26, 2016.

(51) Int. Cl.
| | |
|---|---|
| *C12N 15/113* | (2010.01) |
| *A61P 21/00* | (2006.01) |
| *C12N 15/864* | (2006.01) |
| *C12Q 1/68* | (2018.01) |

(52) U.S. Cl.
CPC ............ *C12N 15/113* (2013.01); *A61P 21/00* (2018.01); *C12N 15/8645* (2013.01); *C12Q 1/68* (2013.01); *C12N 2310/11* (2013.01); *C12N 2320/32* (2013.01); *C12N 2320/33* (2013.01); *C12N 2330/51* (2013.01)

(58) Field of Classification Search
CPC .............. C12N 15/113; C12N 15/8645; C12N 2310/11; C12N 2320/32; C12N 2330/51; A61P 21/00
USPC ..................... 435/6.1, 91.1, 91.31, 455, 458; 514/44 A; 536/23.1, 24.5
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 6,258,595 B1 | 7/2001 | Gao et al. | |
| 6,566,118 B1 | 5/2003 | Atkinson et al. | |
| 2013/0045538 A1 | 2/2013 | Garcia et al. | |
| 2014/0107186 A1 | 4/2014 | Garcia et al. | |

FOREIGN PATENT DOCUMENTS

| | | |
|---|---|---|
| EP | 2426203 A2 | 3/2012 |
| JP | 2013-521791 A | 6/2013 |
| WO | WO-1995/13365 A1 | 5/1995 |
| WO | WO-1995/13392 A1 | 5/1995 |
| WO | WO-1996/17947 A1 | 6/1996 |
| WO | WO-1997/06243 A1 | 2/1997 |
| WO | WO-1997/08298 A1 | 3/1997 |
| WO | WO-1997/09441 A2 | 3/1997 |
| WO | WO-1997/21825 A1 | 6/1997 |
| WO | WO-1998/09657 A2 | 3/1998 |
| WO | WO-1999/011764 A2 | 3/1999 |
| WO | WO-2001/83692 A2 | 11/2001 |
| WO | WO-2002/053703 A2 | 7/2002 |
| WO | WO-2013/016352 A1 | 1/2013 |
| WO | WO-2013/120038 A2 | 8/2013 |

OTHER PUBLICATIONS

Roberts et al (Nature Reviews: Drug Discovery, vol. 19, pp. 673-694 (2020)) (Year: 2020).*
Damase et al (Frontiers in Bioengineering and Biotech., vol. 9, article 628137, pp. 1-24 (2021)) (Year: 2021).*
Kobelt et al (Cancer Gene Therapy in Gene Therapy of Cancer: Methods and Protocols, Methods in Molecular Biology, vol. 2521, pp. 1-15 (Springer Nature 2022)) (Year: 2022).*
Osborn et al (Nucleic Acid Therapeutics, vol. 28, No. 3, pp. 128-136 (2018)) (Year: 2018).*
Bost et al (ACS Nano, vol. 15, pp. 13993-14021 (2021)) (Year: 2021).*
Ansseau et al., DUX4c is up-regulated in FSHD. It induces the MYF5 protein and human myoblast proliferation, *PLoS One.* 4:e7482 (2009).
Carter, Adeno-associated virus vectors, *Curr. Opin. Biotechnol.* 3:533-9 (1992).
Clark et al., A stable cell line carrying adenovirus-inducible rep and cap genes allows for infectivity titration of adeno-associated virus vectors, *Gene. Ther.* 3:1124-32 (1996).

(Continued)

*Primary Examiner* — Jane J Zara

(74) *Attorney, Agent, or Firm* — MARSHALL, GERSTEIN & BORUN LLP

(57) ABSTRACT

The present invention relates to methods for shifting the splicing profile of the DUX4 gene, a double homeobox gene on human chromosome 4q35. Recombinant adeno-associated viruses of the invention deliver DNAs encoding U7-based small nuclear RNAs to induce DUX4 exon-skipping and the expression of shortened forms of DUX4. The methods have application in the treatment of muscular dystrophies such as facioscapulohumeral muscular dystrophy.

6 Claims, 3 Drawing Sheets
Specification includes a Sequence Listing.

(56) References Cited

OTHER PUBLICATIONS

Clark et al., Highly purified recombinant adeno-associated virus vectors are biologically active and free of detectable helper and wild-type viruses, *Hum. Gene. Ther.* 10:1031-9 (1999).
Cserjesi et al., Myogenin induces the myocyte-specific enhancer binding factor MEF-2 independently of other muscle-specific gene products, *Mol. Cell. Biol.* 11:4854-62 (1991).
De et al., High levels of persistent expression of alpha1-antitrypsin mediated by the nonhuman primate serotype rh.10 adeno-associated virus despite preexisting immunity to common human adeno-associated viruses, *Mol. Ther.* 13:67-76 (2006).
Flotte et al., Gene Expression From Adeno-Associated Virus Vectors In Airway Epithelial Cells, *Am J Respir Cell Mol Biol*. 7:349-56 (1992).
Gao et al., Clades of Adeno-associated viruses are widely disseminated in human tissues, *J. Virol.* 78:6381-8 (2004).
GenBank Accession No. AB209345.1, *Homo sapiens* mRNA for atrophin-1 variant protein, Jul. 26, 2016.
Goyenvalle et al., Rescue of dystrophic muscle through U7 snRNA-mediated exon skipping, *Science.* 306:1796-9 (2004).
Hermonat et al., Use of adeno-associated virus as a mammalian DNA cloning vector: transduction of neomycin resistance into mammalian tissue culture cells, *Proc. Natl. Acad. Sci. USA.* 81:6466-70 (1984).
Homma et al., Expression of FSHD-related DUX4-FL alters proteostasis and induces TDP-43 aggregation, *Ann. Clin. Transl. Neurol.* 2:151-66 (2015).
International Preliminary Report on Patentability, PCT/US2017/019422 (Aug. 28, 2018).
International Search Report and Written Opinion, PCT/US2017/19422 (Jul. 14, 2017).
Johnson et al., Muscle creatine kinase sequence elements regulating skeletal and cardiac muscle expression in transgenic mice, *Mol. Cell. Biol.* 9:3393-9 (1989).
Laughlin et al., Cloning of infectious adeno-associated virus genomes in bacterial plasmids, *Gene.* 23:65-73 (1983).
Le Guiner et al., Forelimb treatment in a large cohort of dystrophic dogs supports delivery of a recombinant AAV for exon skipping in Duchenne patients, *Mol. Ther.* 22:1923-35 (2014).
Lebkowski et al., Adeno-associated virus: a vector system for efficient introduction and integration of DNA into a variety of mammalian cell types, *Mol. Cell. Biol.* 8:3988-96 (1988).
Lemmers et al., A unifying genetic model for facioscapulohumeral muscular dystrophy, *Science.* 329:1650-3 (2010).
Mader et al., A steroid-inducible promoter for the controlled overexpression of cloned genes in eukaryotic cells, *Proc. Natl. Acad. Sci. USA.* 90:5603-7 (1993).
Marsic et al., Vector design Tour de Force: integrating combinatorial and rational approaches to derive novel adeno-associated virus variants, *Mol. Ther.* 22:1900-9 (2014).
Marsollier et al., Antisense targeting of 3' end elements involved in DUX4 mRNA processing is an efficient therapeutic strategy for facioscapulohumeral dystrophy: a new gene-silencing approach, *Hum. Mol. Gen.* 1-11 (2016).
McLaughlin et al., Adeno-associated virus general transduction vectors: analysis of proviral structures, *J. Virol.* 62:1963-73 (1988).
Mendell et al., Eteplirsen for the treatment of Duchenne muscular dystrophy, *Ann. Neurol.* 74:637-47 (2013).
Mitsuhashi et al., Expression of DUX4 in zebrafish development recapitulates facioscapulohumeral muscular dystrophy, *Hum. Mol. Genet.* 22:568-77 (2013).
Mori et al., Two novel adeno-associated viruses from cynomolgus monkey: pseudotyping characterization of capsid protein, *Virology.* 330:375-83 (2004).
Muscat et al., Multiple 5'-flanking regions of the human alpha-skeletal actin gene synergistically modulate muscle-specific expression, *Mol. Cell. Biol.* 7:4089-99 (1987).
Muzyczka, Use of adeno-associated virus as a general transduction vector for mammalian cells, *Curr. Top. Microbiol. Immunol.* 158:97-129 (1992).
Neguembor et al., In junk we trust: repetitive DNA, epigenetics and facioscapulohumeral muscular dystrophy, *Epigenomics.* 2:271-87 (2010).
Paul et al., Increased viral titer through concentration of viral harvests from retroviral packaging lines, *Hum. Gene. Ther.* 4:609-45 (1993).
Perrin et al., An experimental rabies vaccine produced with a new BHK-21 suspension cell culture process: use of serum-free medium and perfusion-reactor system, *Vaccine.* 13:1244-50 (1995).
Samulski et al., Cloning of adeno-associated virus into pBR322: rescue of intact virus from the recombinant plasmid in human cells, *Proc. Natl. Acad. Sci. USA.* 79:2077-81 (1982).
Samulski et al., Helper-free stocks of recombinant adeno-associated viruses: normal integration does not require viral gene expression, *J. Virol.* 63:3822-8 (1989).
Schnepp et al., Highly purified recombinant adeno-associated virus vectors. Preparation and quantitation, *Methods Mol. Med.* 69:427-43 (2002).
Schumperli et al., The special Sm core structure of the U7 snRNP: far-reaching significance of a small nuclear ribonucleoprotein, *Cell. Mol. Life. Sci.* 61:2560-70 (2004).
Semenza et al., Hypoxia-inducible nuclear factors bind to an enhancer element located 3' to the human erythropoietin gene, *Proc. Natl. Acad. Sci. USA.* 88:5680-4 (1991).
Senapathy et al., Molecular cloning of adeno-associated virus variant genomes and generation of infectious virus by recombination in mammalian cells, *J. Biol. Chem.* 259:4661-6 (1984).
Snider et al., Facioscapulohumeral dystrophy: incomplete suppression of a retrotransposed gene, *PLoS Genet.* 6:e1001181 (2010).
Srivastava et al., Nucleotide sequence and organization of the adeno-associated virus 2 genome, *J. Virol.* 45:555-64 (1983).
Tratschin et al., A human parvovirus, adeno-associated virus, as a eucaryotic vector: transient expression and encapsidation of the procaryotic gene for chloramphenicol acetyltransferase, *Mol. Cell. Biol.* 4:2072-81 (1984).
Tratschin et al., Adeno-associated virus vector for high-frequency integration, expression, and rescue of genes in mammalian cells, *Mol Cell. Biol.* 5:3251-60 (1985).
Wallace et al., Developing RNAi Therapy for FSHD, *Mol. Ther.* 17(Suppl. 1):S151 (2009).
Wallace et al., DUX4, a candidate gene for facioscapulohumeral muscular dystrophy, causes p53-dependent myopathy in vivo, *Ann. Neurol.* 69:540-52 (2011).
Wallace et al., RNA Interface inhibits DUX4-induced muscle toxicity in vivo: implicaitons for a targeted FSHD therapy, *Mol. Ther.* 20(7):1417-23 (2012).
Wei et al., Therapeutic RNAi for Dominant Muscle Disease, *Mol. Ther.* 17(Suppl. 1):S200 (2009).
Wein et al., Translation from a DMD exon 5 IRES results in a functional dystrophin isoform that attenuates dystrophinopathy in humans and mice, *Nat. Med.* 20:992-1000 (2014).
Weintraub et al., The myoD gene family: nodal point during specification of the muscle cell lineage, *Science.* 251:761-6 (1991).
Wuebbles et al., Testing the effects of FSHD candidate gene expression in vertebrate muscle development, *Int. J. Clin. Exp. Pathol.* 3:386-400 (2010).
Xiao et al., Production of high-titer recombinant adeno-associated virus vectors in the absence of helper adenovirus, *J. Virol.* 72:2224-32 (1998).
Young et al., DUX4 binding to retroelements creates promoters that are active in FSHD muscle and testis, *PLoS Genet.* 9:e1003947 (2013).

\* cited by examiner

Figure 1

SEQ ID NO: 5

```
CCACCCCCCCCCCCACCACCACCACCACCACCCCGCCGGCCGGCCCCAGGCCTCGA    60
CGCCCTGGGTCCCTTCCGGGGTGGGGCGGGCTGTCCCAGGGGGGCTCACCGCCATTCATG  120
AAGGGGTGGAGCCTGCCTGCCTGTGGGCCTTTACAAGGGCGGCTGGCTGGCTGGCTGGCT  180
GTCCGGGCAGGCCTCCTGGCTGCACCTGCCGCAGTGCACAGTCCGGCTGAGGTGCACGGG  240
AGCCCGCCGGCCTCTCTCTGCCCGCGTCCGTCCGTGAAATTCCGGCCGGGGCTCACCGCG  300
ATGGCCCTCCCGACACCCTCGGACAGCACCCTCCCCGCGGAAGCCCGGGGACGAGGACGG  360
CGACGGAGACTCGTTTGGACCCCGAGCCAAAGCGAGGCCCTGCGAGCCTGCTTTGAGCGG  420
AACCCGTACCCGGGCATCGCCACCAGAGAACGGCTGGCCCAGGCCATCGGCATTCCGGAG  480
CCCAGGGTCCAGATTTGGTTTCAGAATGAGAGGTCACGCCAGCTGAGGCAGCACCGGCGG  540
GAATCTCGGCCCTGGCCCGGGAGACGCGGCCCGCCAGAAGGCCGGCGAAAGCGGACCGCC  600
GTCACCGGATCCCAGACCGCCCTGCTCCTCCGAGCCTTTGAGAAGGATCGCTTTCCAGGC  660
ATCGCCGCCGGGAGGAGCTGGCCAGAGAGACGGGCCTCCCGGAGTCCAGGATTCAGATC  720
TGGTTTCAGAATCGAAGGGCCAGGCACCCGGGACAGGGTGGCAGGGCGCCCGCGCAGGCA  780
GGCGGCCTGTGCAGCGCGGCCCCGGCGGGGGTCACCCTGCTCCCTCGTGGGTCGCCTTC   840
GCCCACACCGGCGCGTGGGGAACGGGGCTTCCCGCACCCCACGTGCCCTGCGCGCCTGGG  900
GCTCTCCCACAGGGGGCTTTCGTGAGCCAGGCAGCGAGGGCCGCCCCCGCGCTGCAGCCC  960
AGCCAGGCCGCGCCGGCAGAGGGGATCTCCCAACCTGCCCCGGCGCGCGGGGATTTCGCC 1020
TACGCCGCCCCGGCTCCTCCGGACGGGCGCTCTCCCACCCTCAGGCTCCTCGCTGGCCT  1080
CCGCACCCGGGCAAAAGCCGGGAGGACCGGGACCCGCAGCGCGACGGCCTGCCGGGCCCC 1140
TGCGCGGTGGCACAGCCTGGGCCCGCTCAAGCGGGGCCGCAGGGCCAAGGGGTGCTTGCG 1200
CCACCCACGTCCCAGGGGAGTCCGTGGTGGGGCTGGGGCCGGGGTCCCCAGGTCGCCGGG 1260
GCGGCGTGGGAACCCCAAGCCGGGGCAGCTCCACCTCCCCAGCCCGCGCCCCCGGACGCC 1320
TCCGCCTCCGCGCGGCAGGGGCAGATGCAAGGCATCCCGGCGCCCTCCCAGGCGCTCCAG 1380
GAGCCGGCGCCCTGGTCTGCACTCCCCTGCGGCCTGCTGCTGGATGAGCTCCTGGCGAGC 1440
CCGGAGTTTCTGCAGCAGGCGCAACCTCTCCTAGAAACGGAGGCCCCGGGGGAGCTGGAG 1500
GCCTCGGAAGAGGCCGCCTCGCTGGAAGCACCCCTCAGCGAGGAAGAATACCGGGCTCTG 1560
CTGGAGGAGCTTTAGGACGCGGGGTTGGGACGGGGTCGGGTGGTTCGGGGCAGGGCCGTG 1620
GCCTCTCTTTCGCGGGGAACACCTGGCTGGCTACGGAGGGGCGTGTCTCCGCCCCGCCCC 1680
CTCCACCGGGCTGACCGGCCTGGGATTCCTGCCTTCTAGGTCTAGGCCCGGTGAGAGACT 1740
CCACACCGCGGAGAACTGCCATTCTTTCCTGGGCATCCCGGGGATCCCAGAGCCGGCCCA 1800
GGTACCAGCAGGTGGGCCGCCTACTGCGCACGCGCGGGTTTGCGGGCAGCCGCCTGGGCT 1860
GTGGGAGCAGCCCGGGCAGAGCTCTCCTGCCTCTCCACCAGCCCACCCGCCGCCTGACC  1920
GCCCCCTCCCCACCCCCCACCCCCCACCCCGGAAAACGCGTCGTCCCCTGGGCTGGGTG  1980
GAGACCCCCGTCCCGCGAAACACCGGGCCCCGCGCAGCGTCCGGGCCTGACTCCGCTCCG 2040
GCGGCTCGCCTCCTGTGTGCCCCGCGCCACCGTCGCCCGCCCGCCCGGGCCCCTGCAGC  2100
CTCCCAGCTGCCAGCGCGGAGCTCCTGGCGGTCAAAAGCATACCTCTGTCTGTCTTTGCC 2160
CGCTTCCTGGCTAGACCTGCGCGCAGTGCGCACCCCGGCTGACGTGCAAGGGAGCTCGCT 2220
GGCCTCTCTGTGCCCTTGTTCTTCCGTGAAATTCTGGCTGAATGTCTCCCCCCACCTTCC 2280
GACGCTGTCTAGGCAAACCTGGATTAGAGTTACATCTCCTGGATGATTAGTTCAGAGATA 2340
TATTAAA                                                      2347
```

Chr 4

RECOMBINANT VIRUS PRODUCTS AND METHODS FOR INDUCING DUX4 EXON SKIPPING

CROSS-REFERENCE TO RELATED APPLICATIONS

This application is a continuation application of U.S. patent application Ser. No. 16/079,426, now issued U.S. Pat. No. 11,180,755, which is the U.S. national stage application of International Application No. PCT/US2017/019422, filed Feb. 24, 2017, which claims the benefit of prior U.S. provisional application No. 62/300,500, filed Feb. 26, 2016, the disclosures of which are each incorporated herein by reference in their entireties.

FIELD

The present invention relates to methods for shifting the splicing profile of the DUX4 gene, a double homeobox gene on human chromosome 4q35. Recombinant adeno-associated viruses of the invention deliver DNAs encoding U7-based small nuclear RNAs to induce DUX4 exon-skipping and the expression of shortened forms of DUX4. The methods have application in the treatment of muscular dystrophies such as facioscapulohumeral muscular dystrophy.

Incorporation by Reference of Materials Submitted Electronically

This application contains, as a separate part of disclosure, a Sequence Listing in computer-readable form (filename: 50392A_Seqlisting.TXT; 7,094 bytes—ASCII text file) which is incorporated by reference herein in its entirety.

BACKGROUND

Muscular dystrophies (MDs) are a group of genetic diseases. The group is characterized by progressive weakness and degeneration of the skeletal muscles that control movement. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

Facioscapulohumeral muscular dystrophy (FSHD) is a complex autosomal dominant disorder characterized by progressive and asymmetric weakness of facial, shoulder and limb muscles. Symptoms typically arise in adulthood with most patients showing clinical features before age thirty. About five percent of patients develop symptoms as infants or juveniles and these are generally more severely affected. Clinical presentation can vary from mild (some limited muscle weakness) to severe (wheelchair dependence). Historically, FSHD was classified as the third most common MD, affecting one in 20,000 individuals worldwide. However, recent data indicate FSHD is the most common MD in Europe, suggesting its worldwide incidence may be underestimated.

Typical FSHD cases (FSHD1A, heretofore referred to as FSHD) are linked to heterozygous chromosomal deletions that decrease the copy number of 3.3 kilobase (kb) D4Z4 repeats on human chromosome 4q35. Simplistically, normal individuals have 11-100 tandemly-repeated D4Z4 copies on both 4q35 alleles, while patients with FSHD have one normal and one contracted allele containing 1-10 repeats. In addition FSHD-associated D4Z4 contractions must occur on specific disease-permissive chromosome 4q35 backgrounds (called 4qA). Importantly, no genes are completely lost or structurally mutated as a result of FSHD-associated deletions. Instead, genetic changes associated with FSHD give rise to expression of the toxic DUX4 gene, which is damaging to muscle. FSHD2 (also known as FSHD1B) is phenotypically identical to FSHD1, is associated with DUX4 expression, and requires the 4qA chromosomal background. FSHD2 is not associated with D4Z4 repeat contraction, but is instead caused by mutation in the SMCHD1 gene, which is a chromatin regulator normally involved in repressing the DUX4 locus at 4qA. Mutated SMCHD1 proteins fail to participate in adding heterochromatin to the 4qA DUX4 allele, thereby allowing DUX4 gene expression.

In the leading FSHD pathogenesis models, D4Z4 contractions are proposed to cause epigenetic changes that permit expression of the DUX4 gene. As a result, the aberrant over-expression of otherwise silent or near-silent DUX4 gene, and the genes it regulates, may ultimately cause FSHD. This model is consistent with data showing normal 4q35 D4Z4 repeats have heterochromatin characteristics, while FSHD-linked D4Z4 repeats contain marks more indicative of actively transcribed euchromatin. These transcription-permissive epigenetic changes, coupled with the observation that complete monosomic D4Z4 deletions (i.e., zero repeats) do not cause FSHD, support the hypothesis that D4Z4 repeats harbor potentially myopathic open reading frames (ORFs), which are abnormally expressed in FSHD muscles. This notion was initially considered in 1994, when a D4Z4-localized ORF, called DUX4, was first identified. However, the locus had some characteristics of an unexpressed pseudogene and DUX4 was therefore summarily dismissed as an FSHD candidate. For many years thereafter, the search for FSHD-related genes was mainly focused outside the D4Z4 repeats, and although some intriguing candidates emerged from these studies, no single gene has been conclusively linked to FSHD development. This slow progress led to the re-emergence of DUX4 as an FSHD candidate in 2007. Even as of 2010 though, researchers continued to highlight other genes as candidates. See, for example, Wuebbles et al., *Int. J. Clin. Exp. Pathol.,* 3(4): 386-400 (2010) highlighting the FSHD region gene 1 (frg1). In contrast, Wallace et al., *Mol. Ther.,* 17(Suppl. 1): 5151 (2009); Wei et al., *Mol. Ther.,* 17(Suppl. 1): 5200 (2009); and the Lemmers et al. report from the *Sciencexpress* issue of Aug. 19, 2010 highlight DUX4. Neguembor and Gabellini, *Epigenomics,* 2(2): 271-287 (2010) is a recent review article regarding FSHD.

The role of DUX4 in FSHD pathogenesis can be explained as follows. First, D4Z4 with identical coding regions, and D4Z4 repeats also harbor smaller sense and antisense transcripts, including some resembling microRNAs. Over-expressed DUX4 transcripts and a ~50 kDa full-length DUX4 protein are found in biopsies and cell lines from FSHD patients. These data are consistent with a transcriptional de-repression model of FSHD pathogenesis. In addition, unlike pseudogenes, D4Z4 repeats and DUX4 likely have functional importance, since tandemly-arrayed D4Z4 repeats are conserved in at least eleven different placental mammalian species (non-placental animals lack D4Z4 repeats), with the greatest sequence conservation occurring within the DUX4 ORF. Second, over-expressed DUX4 is toxic to tissue culture cells and embryonic progenitors of developing lower organisms in vivo. This toxicity occurs at least partly through a pro-apoptotic mechanism, indicated by Caspase-3 activation in DUX4 transfected cells, and presence of TUNEL-positive nuclei in developmentally arrested *Xenopus* embryos injected with DUX4 mRNA at the two-cell stage. These findings are consistent with studies showing some pro-apoptotic proteins, including Caspase-3, are present in FSHD patient muscles. In addition to stimulating apoptosis, DUX4 may negatively regulate myogenesis. Human DUX4 inhibits differentiation of mouse C2C12 myoblasts in vitro, potentially by interfering with PAX3 and/or PAX7, and causes developmental arrest and reduced staining of some muscle markers when delivered to progenitor cells of zebrafish or *Xenopus* embryos. Finally, aberrant DUX4 function is directly associated with potentially important molecular changes seen in FSHD patient muscles. Specifically, full-length human DUX4 encodes an approximately 50 kDa double homeodomain transcription factor, and its only known target, Pitx1, was elevated in DUX4 over-expressing FSHD patient muscles. These data support that DUX4 catalyzes numerous downstream molecular changes that are incompatible with maintaining normal muscle integrity.

Splicing modulation using antisense oligonucleotides (AONs) has been developed for the past two decades as a potential treatment for many diseases, most notably Duchene muscular dystrophy (DMD). This includes pre-clinical and clinical trials (Wein et al., *Nat. Med.,* 20:992-1000 (2014) and Mendell et al., *Ann. Neurol.,*74:637-47 (2013). DMD seems well-suited to this type of treatment, since the disease is associated with porous muscle membranes that help permit AON penetration into myofibers. There are no membrane defects in FSHD, and efficient AON delivery may be difficult to achieve. Thus, like any nucleotide-based treatment, delivery of the therapeutic is a major barrier. It is contemplated herein that AAV-based U7-snRNA gene therapy approaches help circumvent these potential delivery problems. The U7-snRNA is normally involved in histone pre-mRNA 3' end processing but it has been modified for exon-skipping. There are three major features to the U7-snRNA system: (1) the U7 promoter to drive expression of the modified snRNA in target cells; (2) an AON inserted in the snRNA backbone, which is designed to base-pair with splice junctions, branch points, or splicing enhancers; (3) a modified sequence (called smOPT) which recruits repressive ribonucleoproteins to the target pre-mRNA and prevents splicing [Schumperli et al., *Cell. and Mol. Life Sciences,* 61:2560-2570 (2004)]. Finally, it is noteworthy that AONs and U7-snRNAs, have proven safe for use in vivo in large animal models of muscular dystrophy [LeGuiner et al., *Mol. Ther.,* 22:1923-1935 (2014)].

Adeno-associated virus (AAV) is a replication-deficient parvovirus, the single-stranded DNA genome of which is about 4.7 kb in length including two 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., *J. Virol.,* 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_001862; at least portions of AAV-7 and AAV-8 genomes are provided in GenBank Accession Nos. AX753246 and AX753249, respectively; the AAVrh74 genome; the AAV-9 genome is provided in Gao et al., *J. Virol.,* 78: 6381-6388 (2004); the AAV-10 genome is provided in *Mol. Ther.,* 13(1): 67-76 (2006); the AAV-11 genome is provided in *Virology,* 330(2): 375-383 (2004); the genome of AAV-12 is provided in GenBank Accession No. DQ813647.1; and the genome of AAV-13 is provided in GenBank Accession No. EU285562.1. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology,* 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

There remains a need in the art for a treatment for muscular dystrophies including FSHD.

SUMMARY

The present invention provides methods and products for preventing or reducing the expression of full-length, toxic DUX4 protein. The methods involve delivering U7-based small nuclear RNAs (snRNAs) specific for the DUX4 gene to cells such as muscle cells. The DUX4 U7-based snRNAs are capable of inducing the expression of non-toxic short isoforms of DUX4 in a cell, e.g., by inducing exon skipping. Use of the methods and products is indicated, for example, in preventing or treating FSHD. Some embodiments of the invention exploit the unique properties of AAV to deliver DNA encoding DUX4 U7-based snRNAs to muscle cells. Other embodiments of the invention utilize other vectors (for example, other viral vectors such as adenovirus, retrovirus, lentivirus, equine-associated virus, alphavirus, pox viruses, herpes virus, polio virus, sindbis virus and vaccinia viruses) to deliver polynucleotides encoding DUX4 U7-based snRNAs.

In one aspect, the invention provides DUX4 U7-based snRNAs capable of inducing the expression of a non-toxic DUX4 short isoform in a cell. In another aspect, the invention provides polynucleotides encoding one or more DUX4 U7-based snRNAs. In another aspect, the invention provides rAAV encoding one or more DUX4 U7-based snRNAs wherein the rAAV lack rep and cap genes. In some embodiments, the DUX4 U7-based snRNA is encoded by the DNA construct hU7-EX1-AS1 (SEQ ID NO: 1) or the DNA construct hU7-EX1-SD (SEQ ID NO: 2).

In another aspect, the invention provides a composition comprising a rAAV encoding one or more DUX4 U7-based snRNAs (for example, a rAAV comprising the DNA set out in SEQ ID NO: 1 or 2) wherein the rAAV lacks rep and cap genes.

In yet another aspect, the invention provides a method of modifying the splicing of the DUX4 gene in a cell comprising contacting the cell with a rAAV encoding one or more DUX4 U7-based snRNAs (for example, a rAAV comprising the DNA set out in SEQ ID NO: 1 or 2) wherein the rAAV lacks rep and cap genes. DUX4 splicing may be modified by at least 10, 20, 30, 40, 50, 60, 70, 80, 90, 95 or 99 percent.

In still another aspect, the invention provides a method of delivering DNA encoding one or more DUX4 U7-based snRNAs to a subject in need thereof, comprising administering to the subject a rAAV encoding one or more DUX4 U7-based snRNAs (for example, a rAAV comprising the DNA set out in SEQ ID NO: 1 or 2) wherein the rAAV lacks rep and cap genes.

In yet another aspect, the invention provides a method of preventing or treating a muscular dystrophy (including, but not limited to, FSHD) comprising administering a rAAV encoding one or ore DUX4 U7-based snRNAs (for example, a rAAV comprising the DNA set out in SEQ ID NO: 1 or 2) wherein the rAAV lacks rep and cap genes. "Treating" includes ameliorating one or more symptoms of the muscular dystrophy (such as FSHD). Molecular, biochemical, histological and functional endpoints demonstrate the therapeutic efficacy of DUX4 U7-based snRNAs. Treatment endpoints contemplated by the invention include, but are not limited to, one or more of: the reduction or elimination of full length DUX4 protein in affected muscles, increase in myofiber diameters, and improvement in muscle strength.

DETAILED DESCRIPTION

Recombinant AAV genomes of the invention comprise one or more AAV ITRs flanking a polynucleotide encoding, for example, one or more DUX4 U7-based snRNAs (i.e., an snRNA that binds to a DUX4 gene sequence and is expressed from a U7 snRNA). The polynucleotide is operatively linked to transcriptional control DNA, specifically promoter DNA that is functional in target cells.

The rAAV genomes of the invention lack AAV rep and cap DNA. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAVrh74, AAV-9, AAV-10, AAV-11, AAV-12 and AAV-13. As noted in the Background section above, the nucleotide sequences of the genomes of various AAV serotypes are known in the art.

DNA plasmids of the invention comprise rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAVrh74, AAV-9, AAV-10, AAV-11, AAV-12 and AAV-13. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014).

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprise a rAAV genome. Embodiments include, but are not limited to, a rAAV including a genome encoding one or more DUX4 U7-based snRNAs, for example, a genome comprising the DNA set out in SEQ ID NO: 1 or the DNA set out in SEQ ID NO: 2, or comprising both DNAs. The genomes of the rAAV lack AAV rep and cap DNA, that is, there is no AAV rep or cap DNA between the ITRs of the genomes.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schenpp and Clark, *Methods Mol. Med.*, 69 427-443 (2002); U.S. Pat. No. 6,566,118 and WO 98/09657.

In another embodiment, the invention contemplates compositions comprising rAAV of the present invention. Compositions of the invention comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg).

Methods of transducing a target cell with rAAV, in vivo or in vitro, are contemplated by the invention. The in vivo methods comprise the step of administering an effective dose, or effective multiple doses, of a composition comprising a rAAV of the invention to a subject (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is FSHD.

Combination treatments/therapies are also contemplated by the invention. Combination as used herein includes both simultaneous treatment or sequential treatments. Combinations of methods of the invention with standard medical treatments (e.g., corticosteroids) are specifically contemplated, as are combinations with novel therapies. Combination therapy with therapies disclosed in International Publication No. WO 2013/016352 are specifically contemplated. International Publication No. WO 2013/016352 is incorporated by reference herein in its entirety.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the DUX4 U7-based snRNAs.

In particular, actual administration of rAAV of the present invention may be accomplished by using any physical method that will transport the rAAV recombinant vector into the target tissue of a subject. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of DUX4 U7-based snRNAs. The present invention thus provides methods of administering/delivering rAAV which express DUX4 U7-based snRNAs to a subject, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family [See Weintraub et al., *Science*, 251: 761-766 (1990], the myocyte-specific enhancer binding factor MEF-2 [Cserjesi and Olson, *Mol Cell Biol* 11: 4854-4862 (1990], control elements derived from the human skeletal actin gene [Muscat et al., *Mol Cell Biol*, 7: 4089-4099 (1987)], the cardiac actin gene, muscle creatine kinase sequence elements [See Johnson et al., *Mol Cell Biol*, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors [Semenza et al., *Proc Natl Acad Sci USA*, 88: 5680-5684 (1990], steroid-inducible elements and promoters including the glucocorticoid response element (GRE) [See Mader and White, *Proc. Natl. Acad. Sci. USA* 90: 5603-5607 (1993)], and other control elements.

Muscle tissue is an attractive target for in vivo DNA delivery, because it is not a vital organ and is easy to access. The invention contemplates sustained expression of one or more U7-based snRNAs from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of one or more DUX4 U7-based snRNAs to a recipient cell either in vivo or in vitro, via a replication-deficient rAAV of the invention resulting in expression of the one or more DUX4 U7-based snRNA by the recipient cell.

Thus, the invention provides methods of administering an effective dose (or doses, administered essentially simultaneously or doses given at intervals) of rAAV that encode one or more DUX4 U7-based snRNAs to a patient in need thereof (e.g., an FSHD patient).

BRIEF DESCRIPTION OF THE DRAWING

FIG. 1 shows the human DUX4 DNA sequence (SEQ ID NO: 5) in which nucleotides 1-300 are the 5' UTR; nucleotides 301-1575 are DUX4 open reading frame (protein coding); nucleotides 1-1582 are Exon 1; nucleotides 1540-1571 are the 779 sequence binding site; nucleotides 1573-1607 are 778 sequence binding site; nucleotides1583-1718 are Intron 1; nucleotides 1719-1811 are Exon 2; nucleotides 1812-2174 are Intron 2; and nucleotides 2175-2347 are Exon 3 sequences ending at poly A site.

FIG. 2A) DUX4 locus in chromosome 4. FIG. 2B) DUX4 transcripts arise from 3 exons (rectangles). DUX4 coding region is shown, where black boxes in exon 1 represent 2 DNA binding domains. Introns are represented by downward pointing lines, polyA signals are identified. FIG. 2C) Structures of the U7 snRNAs and the relative location of each binding sequence in the DUX4-FL transcript shown in B).

FIG. 2A) Full-length DUX4 (DUX4-FL) but not short forms of DUX4 (DUX4-s) caused apoptotic death of HEK293 cells in an Apo-ONE caspase-3/7 assay which measures caspase activity (fluorescent output). FIG. 2B) In an experiment treating HEK293 cells with U7-based snRNA constructs described herein, sequences 778 (hU7-EX1-SD) and 779 (hU7-EX1-AS1) reduced full-length DUX4 protein expression (western blot) and sequence 779

(hU7-EX1-AS1) significantly protected HEK293s from death using a caspase-3/7 assay readout to measure apoptosis.

EXAMPLES

The role of DUX4 in FSHD pathogenesis can be explained as follows. First, D4Z4 repeats are not pseudogenes. The DUX4 locus produces 1.7 kb and 2.0 kb full-length mRNAs with identical coding regions, and D4Z4 repeats also harbor smaller sense and antisense transcripts, including some resembling microRNAs. Over-expressed DUX4 transcripts and a ~50 kDa full-length DUX4 protein are found in biopsies and cell lines from FSHD patients. These data are consistent with a transcriptional de-repression model of FSHD pathogenesis. In addition, unlike pseudogenes, D4Z4 repeats and DUX4 likely have functional importance, since tandemly-arrayed D4Z4 repeats are conserved in at least eleven different placental mammalian species (non-placental animals lack D4Z4 repeats), with the greatest sequence conservation occurring within the DUX4 ORF. Second, over-expressed DUX4 is toxic to tissue culture cells and embryonic progenitors of developing lower organisms in vivo. This toxicity occurs at least partly through a pro-apoptotic mechanism, indicated by Caspase-3 activation in DUX4 transfected cells, and presence of TUNEL-positive nuclei in developmentally arrested Xenopus embryos injected with DUX4 mRNA at the two-cell stage. These findings are consistent with studies showing some pro-apoptotic proteins, including Caspase-3, are present in FSHD patient muscles. In addition to stimulating apoptosis, DUX4 may negatively regulate myogenesis. Human DUX4 inhibits differentiation of mouse C2C12 myoblasts in vitro, potentially by interfering with PAX3 and/or PAX7, and causes developmental arrest and reduced staining of some muscle markers when delivered to progenitor cells of zebrafish or Xenopus embryos. Finally, aberrant DUX4 function is directly associated with potentially important molecular changes seen in FSHD patient muscles. Specifically, full-length human DUX4 encodes an approximately 50 kDa double homeodomain transcription factor, and its only known target, Pitx1, was elevated in DUX4 over-expressing FSHD patient muscles. These data support that DUX4 catalyzes numerous downstream molecular changes that are incompatible with maintaining normal muscle integrity.

Transcriptional de-repression of FSHD is associated with increased expression of the toxic DUX4 transcription factor (the full length, long form), arising from the chromosome 4q subtelomere. This region is normally embedded in heterochromatin and therefore suppressed.

The treatment methods contemplated herein shift the DUX4 splicing profile to favor non-toxic DUX4 (short) forms. This is accomplished by using an antisense exon-skipping strategy designed to block production of toxic, full-length DUX4.

Exemplary aspects and embodiments of the invention are illustrated by the following examples.

Example 1

U7-Based snRNA Constructs for DUX4 Exon Skipping

Figure 2A:
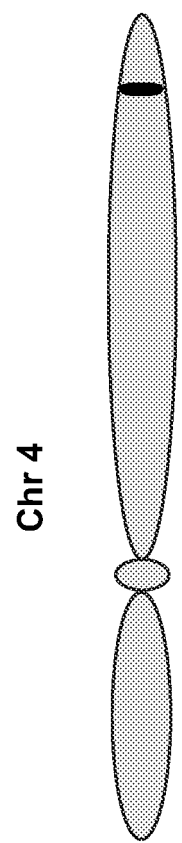
FIGS. 2A-2C show the DUX4 gene structure and U7 snRNA antisense binding locations.

As noted above, FSHD is associated with increased expression of the toxic DUX4 transcription factor from the chromosome 4q subtelomere. This region is normally embedded in heterochromatin and therefore suppressed; in FSHD, deletion of chromatin seeding repetitive elements called D4Z4 repeats (FSHD1; 95% of cases) or mutation in a chromatin modifier gene SMCHD1 (FSHD2; 5%) cause epigenetic changes that de-repress the 4q region and trigger expression of the DUX4 transcription factor (FIGS. 2A and B). Using DUX4 over-expression models, we found that full-length DUX4 (DUX4-FL) causes cell death in vitro and muscle damage in vivo, while a truncated, natural isoform of DUX4 (DUX4s) is non-toxic.

Figure 2B:
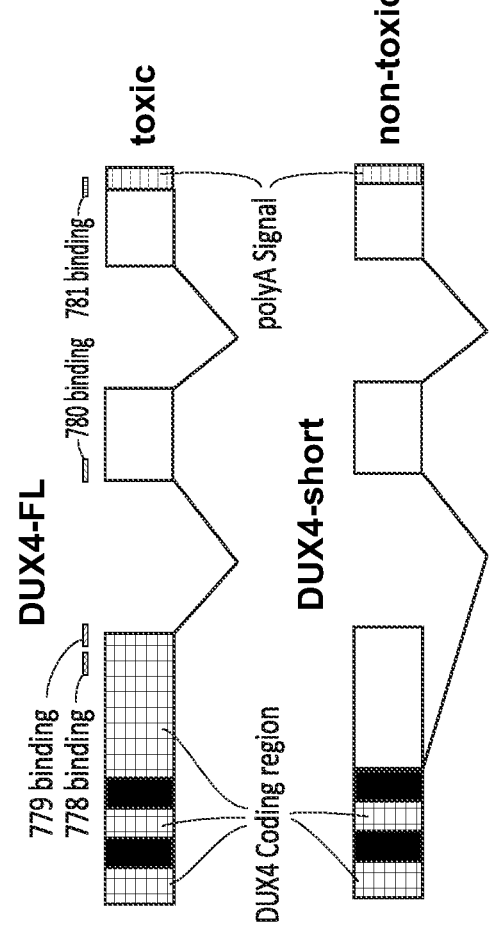
Figure 2C:
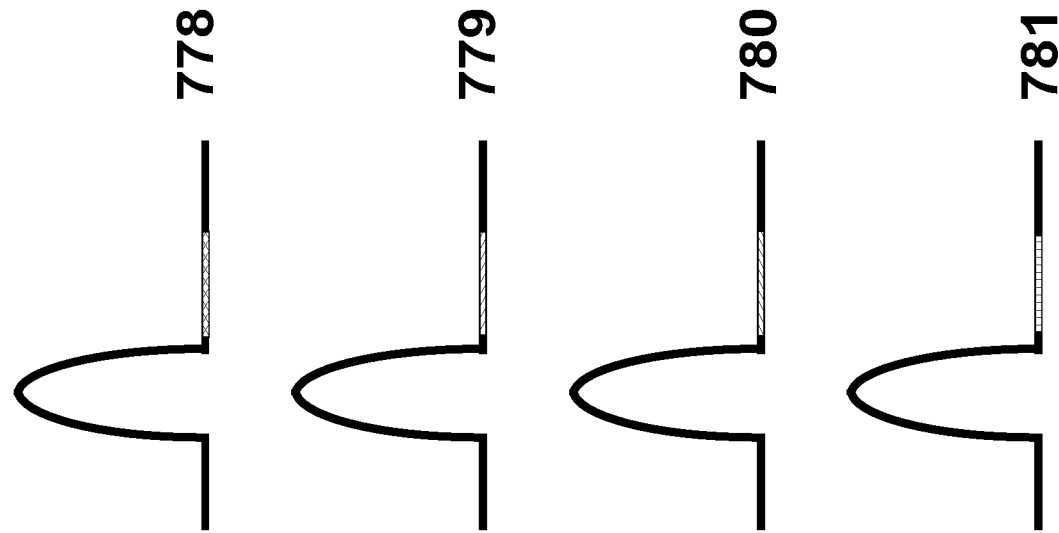
Figure 3A:
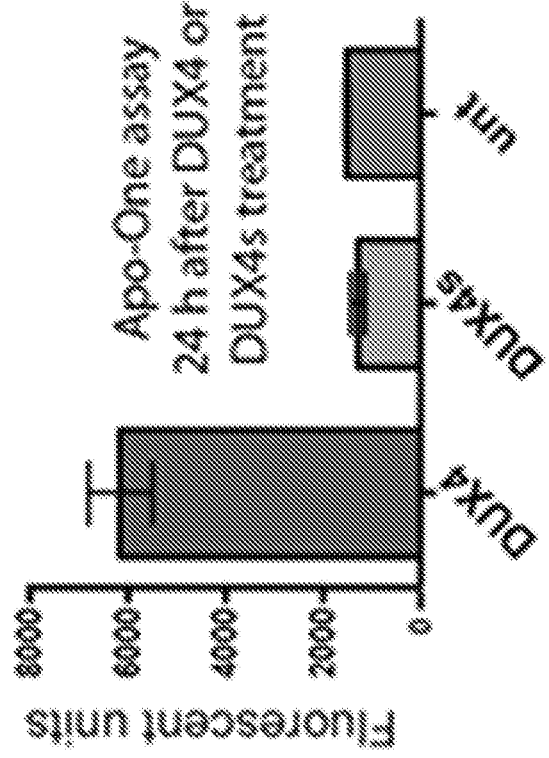
FIGS. 3A-3B show the results of DUX4 cell death and expression assays.
Figure 3B:
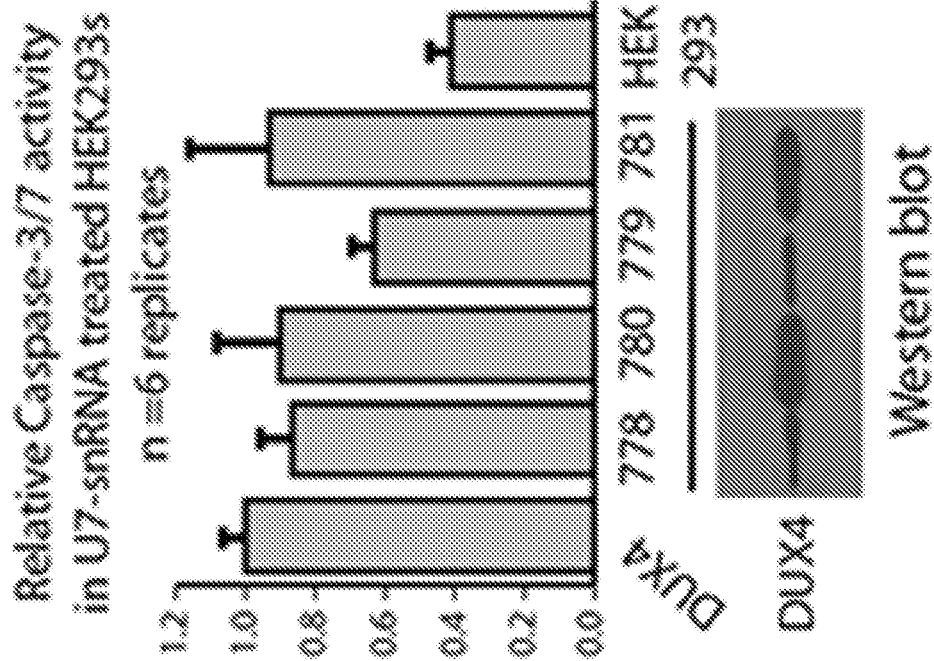

We then designed U7-based snRNAs to prevent splicing of full-length DUX4, or inhibit its polyadenylation (FIG. 2C). U7 snRNA is normally involved in histone pre-mRNA 3' end processing, but mutating the Sm/Lsm protein binding site allows U7 snRNA to become a versatile splicing modulation tool [Young et al., *PLoS Genet* 9(11):e1003947]. We generated U7-based snRNAs designed to block splicing of the DUX4-FL isoform (by masking splice enhancers, splice donors, or splice acceptors), or prevent polyadenylation and de-stabilize the transcript. The DUX4 gene is composed of three exons; the first encodes a full-length DUX4 ORF and the other two are untranslated exons. Exon 3 contains a non-canonical polyA signal that is utilized only in FSHD-permissive muscles. The full length DUX4 ORF encodes a protein containing two DNA binding domains and a C-terminal transactivation domain. This full length protein is toxic to muscles and other tissues/cells. A second isoform has been reported [Snider et al., *Plos Genetics*, 6(10): e1001181 (2010], called DUX4-s (DUX4-short) which arises from the same exon 1 ORF, but this shorter version utilizes an internal splice site which splices out the C-terminal transactivation domain. This shorter version is non-toxic.

We designed U7-based snRNAs to shift the DUX4 splicing profile to favor the benign short form (DUX4s) over the toxic full-length (FL) form. Two U7-based snRNAs were targeted to the splice donor and splice enhancers at the exon 1/intron 1 junction (sequences 778 and 779 below), which will induce DUX4-s production. Sequence 780 was designed to mask the poly-A signal located in exon 3, which would destabilize the DUX4 transcript. We also designed a U7-based snRNA 781 to serve as a negative control. It targets the noncoding exon 3 splice acceptor site and is therefore not expected to affect DUX-FL splicing and toxicity. See FIG. 2. To produce the U7-based snRNAs, we cloned antisense sequences into the human U7 snRNA system used for dystrophin exon skipping [Goyenvalle et al, *Science*, 306(5702):1796-1799 (2004)].

DNAs encoding the U7-based snRNA constructs are set out below. In the sequences, the U7 promoter sequence is double-underlined, the antisense sequences targeting DUX4 are bolded, the SmOPT sequence (binding site for Hnrnpa1) is underlined, the hairpin loop sequence from human U7 snRNA is dotted, and the remaining sequence is the loop structure of U7 transcript.

Sequence 779: hU7-EX1-AS1 (SEQ ID NO: 1)
(bolded antisense sequence binds
to nucleotides 1540-1571 of DUX4 SEQ ID NO: 5)
5'<u>TTTGCTAGCTACTGCCGAATCCAGGTCTCCGGGCTTAACAACAACGAA</u>

-continued

GGGGCTGTGACTGGCTGCTTTCTCAACCAATCAGCACCGAACTCATTTGC

AGTTCCTTAGAATATTATTTTTCCTACTGAAAGTTACCACATGCGTCGTT

AGTTCCTTAGAATATTATTTTTCCTACTGAAAGTTACCACATGCGTCGTT

GTTTATACAGTAATAGGAACAAGAAAAAAGTCACCTAAGCTCACCCTCAT

CAATTGTGGAGTTCCTTTATATCCCATCTTCTCTCCAAACACATACGCAG

AGCTCCTCCAGCAGAGCCCGGTATTCTTCCTCAATTTTTGGAGTAGGCTT

TCTGGCTTTTTACCGGAAAGCCCCTCTTATGATGTTTGTTGCCAATGATA

GATTGTTTTCACTGTGCAAAAATTATGGGTAGTTTTGGTGGTCTTGATGC

AGTTGTAAGCTTGGGGACTAGTTT3'

Sequence 778: hU7-EX1-SD (SEQ ID NO: 2)
(bolded antisense sequence binds to
nucleotides 1573-1607 of DUX4 SEQ ID NO: 5)
5'TTTGCTAGCTACTGCCGAATCCAGGTCTCCGGGCTTAACAACAACGAA

GGGGCTGTGACTGGCTGCTTTCTCAACCAATCAGCACCGAACTCATTTGC

ATGGGCTGAGAACAAATGTTCGCGAACTCTAGAAATGAATGACTTAAGTA

AGTTCCTTAGAATATTATTTTTCCTACTGAAAGTTACCACATGCGTCGTT

GTTTATACAGTAATAGGAACAAGAAAAAAGTCACCTAAGCTCACCCTCAT

CAATTGTGGAGTTCCTTTATATCCCATCTTCTCTCCAAACACATACGCAG

CGAACCACCCGACCCCGTCCCAACCCCGCGTCCTAAATTTTTGGAGTAGG

CTTTCTGGCTTTTTACCGGAAAGCCCCTCTTATGATGTTTGTTGCCAATG

ATAGATTGTTTTCACTGTGCAAAAATTATGGGTAGTTTTGGTGGTCTTGA

TGCAGTTGTAAGCTTGGGGACTAGTTT3'

Sequence 781: hU7EX3-AS1 (SEQ ID NO: 3) (bolded
antisense sequence binds to DUX4 SEQ ID NO:
5, atop the DUX4 intron 2/exon 3 splice junction)
5'TTTGCTAGCTACTGCCGAATCCAGGTCTCCGGGCTTAACAACAACGAA

GGGGCTGTGACTGGCTGCTTTCTCAACCAATCAGCACCGAACTCATTTGC

ATGGGCTGAGAACAAATGTTCGCGAACTCTAGAAATGAATGACTTAAGTA

AGTTCCTTAGAATATTATTTTTCCTACTGAAAGTTACCACATGCGTCGTT

GTTTATACAGTAATAGGAACAAGAAAAAAGTCACCTAAGCTCACCCTCAT

CAATTGTGGAGTTCCTTTATATCCCATCTTCTCTCCAAACACATACGCAG

GCACGTCAGCCGGGGTGCGCACTGCGCGCAGGTCTAGTCAGGAAATTTTT

GGAGTAGGCTTTCTGGCTTTTTACCGGAAAGCCCCTCTTATGATGTTTGT

TGCCAATGATAGATTGTTTTCACTGTGCAAAAATTATGGGTAGTTTTGGT

GGTCTTGATGCAGTTGTAAGCTTGGGGACTAGTTT3'

Sequence 780; hU7-pA-AS (SEQ ID NO: 4)
(bolded antisense sequence binds to
DUX4 SEQ ID NO: 5 atop the DUX4 polyA signal)
5'TTTGCTAGCTACTGCCGAATCCAGGTCTCCGGGCTTAACAACAACGAA

GGGGCTGTGACTGGCTGCTTTCTCAACCAATCAGCACCGAACTCATTTGC

ATGGGCTGAGAACAAATGTTCGCGAACTCTAGAAATGAATGACTTAAGTA

AGTTCCTTAGAATATTATTTTTCCTACTGAAAGTTACCACATGCGTCGTT

GTTTATACAGTAATAGGAACAAGAAAAAAGTCACCTAAGCTCACCCTCAT

CAATTGTGGAGTTCCTTTATATCCCATCTTCTCTCCAAACACATACGCAG

```
GGAGGGGGCATTTTAATATATCTCTGAACTAATTTTTGGAGTAGGCTTTC

TGGCTTTTTACCGGAAAGCCCCTCTTATGATGTTTGTTGCCAATGATAGA

TTGTTTTCACTGTGCAAAAATTATGGGTAGTTTTGGTGGTCTTGATGCAG

TTGTAAGCTTGGGGACTAGTTT3'
```

The constructs were each cloned into a pUC57 plasmid vector backbone.

Example 2

Treatment of Cells with U7-Based snRNA Constructs

The pUC57 plasmid vectors expressing DUX4 and the therapeutic U7-based snRNA constructs were then delivered to HEK293 cells using Lipfectamine-2000, either individually or in combinations, and several outcome measures were examined, including assessment of apoptotic cell death, measurement of DUX4 full-length and DUX4-short gene expression, as well as DUX4-activated biomarkers.

Treatment of DUX4-expressing HEK293 cells with hU7-EX1-AS1 or hU7-EX1-SD reduced full-length DUX4 protein expression as measured by Lowry assay, while hU7-EX1-AS1 significantly protected HEK293 cells from apoptotic cell death, as measured by caspase-3/7 assay (FIG. 2B).

Example 3

Production of rAAV Comprising U7-Based snRNA Constructs rAAV vector was produced by co-transfection in HEK293 cells of three plasmids [pAdhelper, AAV helper, and a rAAV genome containing DUX4 U7-based snRNA construct(s)], followed by cell-harvesting, vector purification, titration, and quality control assays.

Plasmids: pAdhelper contains the adenovirus genes E2A, E4 ORF6, and VA I/II; AAV helper plasmids contain AAV rep2 and cap6 (for example, for an AAV serotype 6 preparation, the capsid gene would be called cap6); the rAAV plasmid contains AAV inverted terminal repeat (ITRs) sequences flanking the U7-based snRNA constructs to be packaged into the vector.

Transfection: Plasmids were transfected into 293 cells (Corning 10-Stack) using CaPO4 at a 4:4:1 ratio (20 ug pAd helper: 20 ug AAV helper: 5 ug rAAV vector plasmid per plate.

Cell harvesting: Forty-eight hr post-transfection, cells were harvested and resuspended in 20 mM Tris (pH 8.0), 1 mM $MgCl_2$ and 150 mM NaCl (T20M1N150) at a density of $5 \times 10^6$ cells/ml. Cells were lysed by four sequential freeze/thaw cycles and Benzonase nuclease (AIC, Stock: 250 U/ul) added to a final concentration of 90 U/ml before cell lysate clarification.

Vector Purification and Titration: Clarified lysates were subjected to iodixanol step gradient purification as previously described (Xiao, X, et al. J. Virol 72:2224-32). The 40% iodixanol layer (containing rAAV) was diluted 5-fold with a no-salt dilution buffer (pH varying depending on serotype) and applied to a Hi-Trap HP-Q/S column. Upon elution with a NaCl salt gradient, peak 1 ml fractions (typically 3-5) were pooled, dialyzed with T20M1N200 (pH 8.0), then sterile filtered and supplemented with 0.001% Pluronic F68. Vector was stored at −80° C. Purified virus was titered for vg using Q-PCR as previously described [Schnepp and Clark, *Methods Mol. Med.*, 69:427-443 (2002)].

Example 4

The effects of the U7-based snRNAs described herein are demonstrated in an FSHD animal model in which the DUX4 gene (coding region+two downstream untranslated exons) is expressed in muscle using adeno-associated viral (AAV) vectors. The FSHD model recapitulates toxic muscle phenotypes that are useful as therapy outcome measures, including Histopathology—rapid development of muscle lesions; presence of central nuclei within 2 weeks, highly variable myofiber sizes Molecular/Biochemical—DUX4 expression; Caspase-3 expression 1,4; downstream biomarker expression (e.g., ZSCAN4)

Functional—muscle strength deficits (e.g., grip strength, specific force)

rAAV comprising one or more U7-based snRNA constructs described herein are co-delivered to animals at 1:1 and 10:1 doses with AAV vectors expressing full-length DUX4 containing all three exons, using our previously published methods [Wallace et al., *Ann. Neurol.*, 69: 540-442 (2011) and Mitsuhashi et al., *Hum. Mol. Genet.*, 22: 568-577 (2012)]. At 1, 2, and 4 weeks following intramuscular injection, outcomes (listed above; initially with n=5 mice planned with additional injections possible) are assessed. The relative amount of DUX4 and DUX4-s is also assessed using real-time PCR approaches.

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety.

We claim:

1. A recombinant adeno-associated virus comprising one or more DUX4 U7-based snRNA construct(s), wherein each construct comprises
    (a) the nucleotide sequence set out in SEQ ID NO: 3;
    (b) the nucleotide sequence set out in SEQ ID NO: 4; or
    (c) the nucleotide sequence set out in SEQ ID NO: 3 and SEQ ID NO: 4.
2. A composition comprising the recombinant adeno-associated virus of claim 1.
3. A nucleic acid comprising
    (a) the nucleotide sequence set out in SEQ ID NO: 3;
    (b) the nucleotide sequence set out in SEQ ID NO: 4; or
    (c) the nucleotide sequence set out in SEQ ID NO: 3 and SEQ ID NO: 4.
4. The recombinant adeno-associated virus of claim 1, wherein the virus lacks rep and cap genes.
5. The recombinant adeno-associated virus of claim 1, wherein the RNA encoded by the DUX4 U7-based snRNA construct is capable of inducing the expression of a non-toxic DUX4 short isoform in a cell.
6. The recombinant adeno-associated virus of claim 1, wherein the adeno-associated virus is AAV1, AAV2, AAV3, AAV4, AAV5, AAV6, AAV7, AAV8, AAV9, AAV10, AAV11, AAV12, AAV13, or AAVrh74.

* * * * *

SEQUENCE LISTING

<160> NUMBER OF SEQ ID NOS: 5

<210> SEQ ID NO 1
<211> LENGTH: 472

```
<212> TYPE: DNA
<213> ORGANISM: Homo sapiens

<400> SEQUENCE: 1
tttgctagct actgccgaat ccaggtctcc gggcttaaca acaacgaagg ggctgtgact      60
ggctgctttc tcaaccaatc agcaccgaac tcatttgcat gggctgagaa caaatgttcg     120
cgaactctag aaatgaatga cttaagtaag ttccttagaa tattatttt cctactgaaa      180 gttaccacat gcgtcgttgt ttatacagta ataggaacaa gaaaaaagtc acctaagctc     240
accctcatca attgtggagt tcctttatat cccatcttct ctccaaacac atacgcagag     300
ctcctccagc agagcccggt attcttcctc aattttggga gtaggcttc tggcttttta      360 ccggaaagcc cctcttatga tgtttgttgc caatgataga ttgttttcac tgtgcaaaaa     420
ttatgggtag ttttggtggt cttgatgcag ttgtaagctt ggggactagt tt             472

<210> SEQ ID NO 2
<211> LENGTH: 475
<212> TYPE: DNA
<213> ORGANISM: Homo sapiens

<400> SEQUENCE: 2
tttgctagct actgccgaat ccaggtctcc gggcttaaca acaacgaagg ggctgtgact      60
ggctgctttc tcaaccaatc agcaccgaac tcatttgcat gggctgagaa caaatgttcg     120
cgaactctag aaatgaatga cttaagtaag ttccttagaa tattatttt cctactgaaa      180 gttaccacat gcgtcgttgt ttatacagta ataggaacaa gaaaaaagtc acctaagctc     240
accctcatca attgtggagt tcctttatat cccatcttct ctccaaacac atacgcagcg     300
aaccacccga ccccgtccca accccgcgtc ctaaattttt ggagtaggct ttctggcttt     360
ttaccggaaa gccctcttta tgatgtttgt tgccaatgat agattgtttt cactgtgcaa     420
aaattatggg tagttttggt ggtcttgatg cagttgtaag cttggggact agttt          475

<210> SEQ ID NO 3
<211> LENGTH: 483
<212> TYPE: DNA
<213> ORGANISM: Homo sapiens

<400> SEQUENCE: 3
tttgctagct actgccgaat ccaggtctcc gggcttaaca acaacgaagg ggctgtgact      60
ggctgctttc tcaaccaatc agcaccgaac tcatttgcat gggctgagaa caaatgttcg     120
cgaactctag aaatgaatga cttaagtaag ttccttagaa tattatttt cctactgaaa      180 gttaccacat gcgtcgttgt ttatacagta ataggaacaa gaaaaaagtc acctaagctc     240
accctcatca attgtggagt tcctttatat cccatcttct ctccaaacac atacgcaggc     300
acgtcagccg gggtgcgcac tgcgcgcagg tctagtcagg aaattttgg agtaggcttt      360 ctggcttttt accggaaagc cctcttatg atgtttgttg ccaatgatag attgttttca      420
ctgtgcaaaa attatgggta gttttggtgg tcttgatgca gttgtaagct tggggactag     480
ttt                                                                   483

<210> SEQ ID NO 4
<211> LENGTH: 470
<212> TYPE: DNA
<213> ORGANISM: Homo sapiens

<400> SEQUENCE: 4
```

| | |
|---|---|
| tttgctagct actgccgaat ccaggtctcc gggcttaaca acaacgaagg ggctgtgact | 60 |
| ggctgctttc tcaaccaatc agcaccgaac tcatttgcat gggctgagaa caaatgttcg | 120 |
| cgaactctag aaatgaatga cttaagtaag ttccttagaa tattattttt cctactgaaa | 180 |
| gttaccacat gcgtcgttgt ttatacagta ataggaacaa gaaaaaagtc acctaagctc | 240 |
| accctcatca attgtggagt tcctttatat cccatcttct ctccaaacac atacgcaggg | 300 |
| agggggcatt ttaatatatc tctgaactaa ttttttggagt aggctttctg gcttttttacc | 360 |
| ggaaagcccc tcttatgatg tttgttgcca atgatagatt gttttcactg tgcaaaaatt | 420 |
| atgggtagtt ttggtggtct tgatgcagtt gtaagcttgg ggactagttt | 470 |

```
<210> SEQ ID NO 5
<211> LENGTH: 2347
<212> TYPE: DNA
<213> ORGANISM: Homo sapiens
<220> FEATURE:
<221> NAME/KEY: 5'UTR
<222> LOCATION: (1)..(300)
<220> FEATURE:
<221> NAME/KEY: misc_feature
<222> LOCATION: (1)..(1582)
<223> OTHER INFORMATION: Exon 1
<220> FEATURE:
<221> NAME/KEY: misc_feature
<222> LOCATION: (301)..(1575)
<223> OTHER INFORMATION: DUX4 open reading frame (protein coding)
<220> FEATURE:
<221> NAME/KEY: misc_binding
<222> LOCATION: (1540)..(1571)
<223> OTHER INFORMATION: 779 sequence binding site
<220> FEATURE:
<221> NAME/KEY: misc_binding
<222> LOCATION: (1573)..(1607)
<223> OTHER INFORMATION: 778 sequence binding site
<220> FEATURE:
<221> NAME/KEY: Intron
<222> LOCATION: (1583)..(1718)
<223> OTHER INFORMATION: Intron 1
<220> FEATURE:
<221> NAME/KEY: misc_feature
<222> LOCATION: (1719)..(1811)
<223> OTHER INFORMATION: Exon 2
<220> FEATURE:
<221> NAME/KEY: Intron
<222> LOCATION: (1812)..(2174)
<223> OTHER INFORMATION: Intron 2
<220> FEATURE:
<221> NAME/KEY: misc_feature
<222> LOCATION: (2175)..(2347)
<223> OTHER INFORMATION: Exon 3
```

<400> SEQUENCE: 5

| | |
|---|---|
| ccacccccc cccccaccac caccaccacc accacccgc cggccggccc caggcctcga | 60 |
| cgccctgggt cccttccggg gtggggcggg ctgtcccagg ggggctcacc gccattcatg | 120 |
| aaggggtgga gcctgcctgc ctgtgggcct ttacaagggc ggctggctgg ctggctggct | 180 |
| gtccgggcag gcctcctggc tgcacctgcc gcagtgcaca gtccggctga ggtgcacggg | 240 |
| agcccgccgg cctctctctg cccgcgtccg tccgtgaaat tccggccggg gctcaccgcg | 300 |
| atggccctcc cgacaccctc ggacagcacc ctccccgcgg aagcccgggg acgaggacgg | 360 |
| cgacggagac tcgtttggac cccgagccaa agcgaggcc tgcgagcctg ctttgagcgg | 420 |
| aacccgtacc cgggcatcgc caccagagaa cggctggccc aggccatcgg cattccggag | 480 |
| cccagggtcc agatttggtt tcagaatgag aggtcacgcc agctgaggca gcaccggcgg | 540 |
| gaatctcggc cctggcccgg gagacgcggc ccgccagaag gccggcgaaa gcggaccgcc | 600 |

```
gtcaccggat cccagaccgc cctgctcctc cgagcctttg agaaggatcg ctttccaggc    660
atcgccgccc gggaggagct ggccagagag acgggcctcc cggagtccag gattcagatc    720
tggtttcaga atcgaagggc caggcacccg ggacagggtg gcagggcgcc cgcgcaggca    780
ggcggcctgt gcagcgcggc ccccggcggg ggtcaccctg ctccctcgtg ggtcgccttc    840
gcccacaccg gcgcgtgggg aacggggctt cccgcacccc acgtgccctg cgcgcctggg    900
gctctcccac agggggcttt cgtgagccag gcagcgaggg ccgcccccgc gctgcagccc    960
agccaggccg cgccggcaga ggggatctcc caacctgccc cggcgcgcgg ggatttcgcc   1020
tacgccgccc cggctcctcc ggacggggcg ctctcccacc ctcaggctcc tcgctggcct   1080
ccgcacccgg gcaaaagccg ggaggaccgg gacccgcagc gcgacggcct gccgggcccc   1140
tgcgcggtgg cacagcctgg gcccgctcaa gcggggccgc agggccaagg ggtgcttgcg   1200
ccacccacgt cccaggggag tccgtggtgg ggctggggcc ggggtcccca ggtcgccggg   1260
gcggcgtggg aacccaagc cggggcagct ccacctcccc agcccgcgcc cccggacgcc   1320
tccgcctccg cgcggcaggg gcagatgcaa ggcatcccgg cgccctccca ggcgctccag   1380
gagccggcgc cctggtctgc actcccctgc ggcctgctgc tggatgagct cctggcgagc   1440
ccggagtttc tgcagcaggc gcaacctctc ctagaaacgg aggcccccggg ggagctggag   1500 gcctcggaag aggccgcctc gctggaagca cccctcagcg aggaagaata ccgggctctg   1560
ctggaggagc tttaggacgc ggggttggga cggggtcggg tggttcgggg cagggccgtg   1620
gcctctcttt cgcggggaac acctggctgg ctacggaggg gcgtgtctcc gccccgcccc   1680
ctccaccggg ctgaccggcc tgggattcct gccttctagg tctaggcccg gtgagagact   1740
ccacaccgcg gagaactgcc attctttcct gggcatcccg gggatcccag agccggccca   1800
ggtaccagca ggtgggccgc ctactgcgca cgcgcgggtt tgcgggcagc cgcctgggct   1860
gtgggagcag cccgggcaga gctctcctgc ctctccacca gcccacccca ccgcctgacc   1920 gcccctccc cacccccac cccccacccc cggaaaacgc gtcgtcccct gggctgggtg   1980
gagacccccg tcccgcgaaa caccgggccc cgcgcagcgt ccgggcctga ctccgctccg   2040
gcggctcgcc tcctgtgtgc ccccgcgcca ccgtcgcccg cccgcccggg cccctgcagc   2100
ctcccagctg ccagcgcgga gctcctggcg gtcaaaagca tacctctgtc tgtctttgcc   2160
cgcttcctgg ctagacctgc gcgcagtgcg caccccggct gacgtgcaag ggagctcgct   2220
ggcctctctg tgcccttgtt cttccgtgaa attctggctg aatgtctccc cccaccttcc   2280
gacgctgtct aggcaaacct ggattagagt tacatctcct ggatgattag ttcagagata   2340
tattaaa                                                             2347
```